United States Patent
Wilke et al.

[11] Patent Number: 6,039,697
[45] Date of Patent: Mar. 21, 2000

[54] FIBER OPTIC BASED MULTICOMPONENT INFRARED RESPIRATORY GAS ANALYZER

[75] Inventors: Thomas A. Wilke, Boulder; Ziyi Wang, Louisville, both of Colo.

[73] Assignee: Datex-Ohmeda, Inc., Louisville, Colo.

[21] Appl. No.: 09/045,453

[22] Filed: Mar. 20, 1998

[51] Int. Cl.[7] ............... A61B 5/00; A61B 5/08; G01J 5/00; G01J 5/02
[52] U.S. Cl. ............ 600/532; 600/310; 250/338.1; 250/339.13; 250/343
[58] Field of Search ............ 600/532, 529, 600/310, 473, 476; 250/338.1, 339.01, 339.13, 343

[56] References Cited

U.S. PATENT DOCUMENTS

| | | |
|---|---|---|
| 3,465,753 | 9/1969 | Levy et al. . |
| 4,003,707 | 1/1977 | Lübbers et al. ............ 600/310 |
| 4,067,320 | 1/1978 | Olsson et al. ............ 600/532 |
| 4,180,734 | 12/1979 | Gedeon ............ 250/345 |
| 4,746,218 | 5/1988 | Lord, III ............ 356/437 |
| 4,928,703 | 5/1990 | Wong ............ 600/532 |
| 5,067,492 | 11/1991 | Yelderman et al. ............ 600/532 |
| 5,081,998 | 1/1992 | Yelderman et al. ............ 600/532 |
| 5,095,913 | 3/1992 | Yelderman et al. ............ 600/532 |
| 5,272,090 | 12/1993 | Gavish et al. ............ 600/317 |
| 5,282,473 | 2/1994 | Braig et al. ............ 600/532 |
| 5,738,106 | 4/1998 | Yanamori et al. ............ 600/532 |

FOREIGN PATENT DOCUMENTS

| | | |
|---|---|---|
| 0 309 666 A1 | 4/1989 | European Pat. Off. . |
| 27 07 090 A1 | 8/1978 | Germany . |

*Primary Examiner*—Cary O'Connor
*Assistant Examiner*—Navin Natnithithadha
*Attorney, Agent, or Firm*—Holme Roberts & Owen LLP

[57] ABSTRACT

A novel respiratory gas analyzer employs optical fibers to facilitate in-stream, multiple component infrared analysis. In one embodiment, the analyzer (10) includes an infrared source (12), entrance optics (14), a sample chamber (20), exit optics (24) and a detector assembly (28). One or both of the entrance optics (14) and exit optics (24) includes infrared optical fibers. In this manner, the source (12) and or detector assembly (28) can be located away from the patient (22) as may be desired. In addition, the fiber optic implementation reduces system complexity and optical alignment concerns.

36 Claims, 5 Drawing Sheets

FIBER OPTIC BASED MULTICOMPONENT INFRARED RESPIRATORY GAS ANALYZER

FIELD OF THE INVENTION

The present invention relates generally to spectral gas analysis and, in particular to an apparatus and method for determining the composition of a multicomponent respiratory gas stream using infrared fiber optics.

BACKGROUND OF THE INVENTION

There are many commercial applications in which it is desirable to monitor the concentrations of components in gas streams. In particular, it is important for medical personnel to monitor the concentrations of the various components in a patient's respiratory stream to dispense the proper amount of medication and/or identify potentially hazardous conditions. This is especially important in the field of anesthesiology, where gaseous anesthetic or therapeutic agents, such as nitrous oxide, halothane, enflurane, desflurane, sevoflurane, and isoflurane, are dispensed to the patient in controlled dosages. Therefore, monitoring anesthesia may involve analyzing the respiratory stream with respect to one or more components, possibly including anesthetic or therapeutic agents, as well as other respiratory gases, such as carbon dioxide.

Spectral gas analyzers provide an indication of the presence and concentration of selected components in a gas sample based on the detected spectral composition of light transmitted through the gas sample. The gaseous components of interest can be characterized with regard to specific light absorption properties. For example, a particular gaseous component may be characterized by an absorption band at a particular wavelength or over a wavelength range. By comparing the intensity of transmitted and received light of a selected wavelength or range of wavelengths for a particular gas sample, information regarding the absorption characteristics and composition of the sample can be obtained. To monitor multiple gaseous components, some spectral gas analyzers employ multiple light sources, multiple optical filters, and/or multiple light detectors.

Spectral measurement errors may arise from variations in the optics and the optical path between the source and detector and variations in detector response. Minimizing such sources of potential error is crucial in many applications, such as monitoring respiratory and anesthetic gases.

With regard to potential optical sources of error, many spectral gas analyzers utilize lenses, mirrors, and other conventional optical elements to direct light from a source through a sample to a detector. Although it may be desirable to have a relatively long light path between the source and the detector to improve optical wavelength resolution, the light intensity can be significantly decreased due to losses along the light path. At the same time, it is desirable to have a compact instrument. To save space, the optical path may be folded by using multiple mirrors to reflect light beams between the source and the sample. Proper and consistent alignment of these lenses and mirrors relative to the source, sample, and detector is often critical for consistent and accurate spectral measurements. Keeping the surfaces of mirrors and lenses clean and free from scratches and other defects is also important.

Other sources of potential error relate to the analyzer environment. Infrared sources, such as are used in spectral gas analyzers, generally produce significant heat, which may adversely affect the stability and/or performance of other components in the analyzer, such as detectors. Further, the temperature variations cause pressure/volume changes and, therefore, variations in the absorption characteristics of the analyzed gases. It is therefore desirable to separate the infrared source from the sample and/or detector to reduce temperature fluctuations in the detector and/or sample.

In addition to eliminating sources of error in spectral gas analyzers, it is desirable to limit the number of active components, such as optical elements in the light path, thereby simplifying analyzer design, reducing costs, increasing reliability, and simplifying calibration procedures. At the same time, it is desirable to reduce analyzer size for many applications where space is limited. It is also advantageous to situate the analyzer away from the immediate vicinity of the patient to allow health care personnel to move and work with the patient, where space is typically at a premium. In this regard, analyzers should be structurally robust so as to minimize mechanical recalibration and realignment of optical components and provide for a high level of mechanical reliability.

SUMMARY OF THE INVENTION

It is an object of the present invention to provide a spectral gas analyzer for a respiratory gas sample that is both highly accurate and reliable in determining the type and/or amount of components in the sample, particularly for anesthetic components.

It is another object of the present invention to provide a spectral gas analyzer that is structurally robust, has a rugged construction, and minimizes the need for mechanical realignment and recalibration of the analyzer.

It is a further object of the present invention to provide a spectral gas analyzer that allows for infrared analysis of a respiratory stream in close proximity to the patient.

It is still a further object of the present invention to provide a spectral gas analyzer that allows for infrared analysis of a respiratory sample in-stream, thereby simplifying analyzer design and reducing sample disposal concerns.

It is yet another object of the present invention to provide a spectral gas analyzer utilizing a probe to convey light to and from a sample gas chamber which contains the respiratory gas, with the probe being physically separable from the chamber.

It is a further object of the present invention to provide a spectral gas analyzer having an infrared source which is thermally isolated from other, temperature-sensitive components, with reduced light intensity losses between the source and the sample and detector or detectors.

It is yet a further object of the present invention to provide a spectral gas analyzer that can be situated away from the immediate vicinity of the patient to allow health care personnel to move and work with the patient in space restricted areas.

Yet other objects are to provide a spectral gas analyzer that is inexpensive and simple to use.

These and other objectives are addressed by the spectral gas analyzer of the present invention.

The present invention is directed to an apparatus for analyzing respiratory gases and related methodology. The apparatus incorporates a conduit or chamber through which the respiratory gases can flow and which has at least one wall portion which is substantially transparent to infrared light. Preferably, the chamber is directly incorporated into a patient respiratory circuit and does not require diversion of a portion of the respiratory stream for analysis. The apparatus also includes fiber optics for transmitting infrared light between a source and the conduit or chamber and/or transmitting infrared light from the conduit or chamber to one or more detectors. The fiber optics may be associated with additional optical elements, such as lenses, mirrors, prisms, or diffraction devices to focus and/or direct light. The fiber optics, the transparent portion of the conduit wall, any other optical elements present in the infrared light path, and the detector are all capable of transmitting and/or receiving infrared light having the wavelengths of interest for the components being analyzed.

The apparatus is adapted for light transmission through the gas in the conduit or chamber. Infrared light may be transmitted through the conduit via two or more substantially transparent wall portions. Alternatively, infrared light entering the conduit may be reflected by a mirror, thus making at least two passes through the gas in the conduit. Also alternatively, an unshielded fiber optics light guide may pass through a portion of the conduit. In this case, Fourier transform analysis can be utilized to determine the gas composition based on the interaction of infrared light with the gas at the light guide/gas interface in the conduit.

By utilizing fiber optics, the source, sample conduit or chamber, and/or the detector assembly can be located away from each other. The fiber optics therefore facilitate in stream analysis in proximity to the patient for enhanced response and accuracy while allowing various system components to be remotely located. Moreover, the ability to separate components is useful in avoiding overheating of temperature-sensitive system components and allowing more room for health care personnel to perform their duties. The use of fiber optics reduces the need for mechanical realignment and recalibration of elements in the optical path between the light source and the detector assembly and also reduces the complexity of the apparatus relative to systems utilizing conventional optics. Thus, the size of the apparatus can be reduced, while maintaining high accuracy and reliability in the system. In addition, the use of fiber optics allows a longer light path without a significant reduction in light intensity.

In addition to normal respiratory gases, such as carbon dioxide, nitrogen, and oxygen, the respiratory gas side stream may comprise anesthetic agents and/or therapeutic agents, such as nitrous oxide, halothane, enflurane, desflurane, sevoflurane, and isoflurane. The system of the present invention is particularly suitable for monitoring carbon dioxide and anesthetic or therapeutic agents in respiratory gases. These components each have a distinctive infrared absorption spectrum in the mid-infrared range and absorb light at wavelengths having high rates of detection by the analyzing means. A preferred wavelength for detection of these components is between about 2 and about 12 microns. In this regard, the sample is preferably analyzed at least over the 4–8 micron range and, more preferably, over at least the 4–10 micron range.

Although each of the component gaseous compounds has a distinctive infrared absorption spectrum, individual absorption peaks of different gases may overlap. Further, other materials, such as water and materials formed by chemical interaction of various components in system filters and the like, may be present in the light path and have spectra which overlap peaks of the components to be analyzed. Thus, it is desirable to evaluate the overall absorption spectrum of the mixture in a way that allows determination of one or more components in the presence of other components with overlapping absorption peaks.

According to one aspect of the present invention, the fiber optics-based apparatus is suitable for mainstream monitor applications, i.e., for making respiratory gas measurements at a sample area of a respiratory stream outside the patient. In this regard, the sample area may include a respiratory gas conduit having a wall portion outside the patient which is substantially transparent to infrared light. The fiber optics are also positioned outside the patient, allowing for a variety of optical configurations, including transmission through the sample area of the conduit, reflection within the sample area of the conduit, or passing the fiber optics through the sample area of the conduit for use with Fourier transform analysis, as described above.

According to another aspect of the present invention, the apparatus is useful for monitoring multiple gaseous components present in a respiratory gas stream. In this regard, the apparatus includes an infrared source and fiber optics suitable for transmitting the infrared light and a processor for analyzing the transmitted light relative to the multiple gaseous components. The fiber optics are positioned for light transmission along a light path between the source and the detector, with the sample conduit positioned in or along the light path.

In one embodiment, the infrared source produces light over a broad band of infrared wavelengths, including wavelengths at which the gaseous components of interest have identifying features in their absorption spectra. In this regard, the source preferably provides, and the fiber optics are preferably suitable for transmitting, light distributed across the mid-infrared portion of the spectrum, i.e., between about 4–8 microns in wavelength. More preferably, the source produces light over a continuum of infrared wavelengths in the mid-infrared range. By providing broad band infrared light, including a range of infrared wavelengths, in combination with a suitable detector assembly, the system can be used to monitor mixtures of these respiratory gases, and it can be easily adapted to monitor mixtures including different or additional components in varying relative concentrations.

In another embodiment, the source provides infrared light, and the light path includes an unshielded fiber optics light guide passing through the sample conduit. A portion of the light passing through the light guide interacts with the respiratory gas in the conduit, resulting in variations in the light transmitted along the light guide. Preferably, the light intensity of the source is modulated to allow detection via Fourier transform analysis of the transmitted light as affected by the interactions at the lightguide/gas interface. More preferably, the light intensity is modulated in a sinusoidal pattern.

In another aspect of the present of invention, the apparatus includes a broad band infrared light source and a detector assembly capable of detecting infrared light transmitted by the fiber optics and having wavelengths within the broad band. The detector assembly preferably includes one or more filters for receiving the broad band light and defining a plurality of infrared wavelength bands, and one or more detectors for detecting the infrared wavelength bands. The detector assembly may further include one or more electronic elements, such as a microprocessor or computer, for analyzing data output by the detectors. Preferably, the electronic element or elements are also capable of displaying the analysis results in real time in a format that is readily usable by medical personnel.

In this regard, the filter may comprise one or more polychromatic filters which filter the broad band infrared light to provide a plurality of narrow wavelength bands, with each narrow band including a different portion of the range of wavelengths produced by the source and over which the respiratory gas is to be analyzed. Each narrow band may include wavelengths corresponding to one or more absorption peaks of individual gas components or to a portion of the overall spectrum in which there is no significant absorption by any component of the gas. Preferably, the system includes a variable filter, which passes different wavelength bands at different physical locations on the filter. A particularly suitable type of polychromatic filter for use with the detectors is a linear variable filter.

The individual detectors in the detector assembly each detect light in one or more of the narrow bands formed by the filter or filters. Thus, by including one or more filters and a plurality of detectors, a plurality of portions of the overall gas absorption spectrum can be observed, making it possible to determine the contributions of individual gas components to the overall spectrum. In this regard, there preferably are more narrow wavelength bands and more individual detectors than there are components to be analyzed, allowing absorption measurements to be obtained for narrow wavelength bands corresponding to more than one absorption peak for individual sample components. By overdetermining the system in this manner, it is possible to separate accurately the contributions of individual components to the overall spectrum.

In yet another aspect of the present invention, the apparatus comprises a fiber optics probe which conveys infrared light to and from a sample chamber through which respiratory gas can flow. The probe is adapted to interface with the sample chamber so as to allow for the desired optical gas analysis. Preferably, the probe is readily attachable and detachable relative to the sample chamber as may be desired. The probe is adapted for optical alignment with the sample chamber such that light transmitted through the probe to the chamber passes through the chamber and is transmitted away from the chamber by the probe, such as to a detector assembly.

The sample chamber may be in the form of a tube which extends from a patient's mouth and has a wall adapted for transmission of infrared light between the interior and the exterior of the tube. Thus, the probe may have an end which engages the tube where the wall is adapted for light transmission. A portion of the probe may extend into the tube, and the extending portion may include one or more lenses or mirrors for directing light from the chamber back into the probe. Alternatively, the probe may support transmitting and receiving elements in optical alignment on opposite sides of the sample chamber such that the light is directed in a single direction through the sample chamber between the elements. As a further alternative, the extending portion may include a light guide extending longitudinally through the tube, such as for use with Fourier transform analysis, as described above. Preferably, upon detaching the probe, the tube is disposable or easily cleaned for re-use. The fiber optics used for light transmission to and from the sample chamber may be in the form of two fiber optics light guides, one transmitting light in each direction. The two light guides may be arranged concentrically. Alternatively, separate light guides may be utilized.

Thus, the system of the present invention includes a reduced number of active system components and can provide accurate gas sample analysis, including multiple component or polychromatic analysis of respiratory and anesthetic gases. The invention reduces sources of potential error, reduces size and weight requirements, and enhances accuracy and reliability of the analysis. The invention also facilitates multicomponent infrared analysis in the respiratory stream proximate to the patient.

The spectral analyzer described above can have a number of desirable features. The analyzer can be relatively lightweight and compact, thereby permitting the analyzer to be used by emergency medical personnel, transported and positioned with the patient, and/or placed easily in space restricted areas. The analyzer can have a relatively robust and rugged construction due to its simple design and use of few, if any, moving parts. The use of fiber optics provides for a high degree of mechanical reliability and reduces the need for careful alignment of numerous elements of the light path or paths. The use of fiber optics and analysis of a stream permit the analyzer to be located some distance away from the gas stream, thereby avoiding loss of light intensity, overheating of temperature-sensitive components, and clutter, such as adjacent a patient undergoing a medical procedure under general anesthesia, where space is at a premium. The analyzer can be constructed with relatively inexpensive materials, have a relatively low assembly cost, and be adapted for ease of use. The analyzer can be readily adapted for the detection and measurement of multiple selected components of the gas sample, including new anesthetic gases.

DETAILED DESCRIPTION

The gas analyzer of the present invention both detects the presence and measures the concentration of analytes contained in a gas sample that is passed through a sample gas chamber, such as a respiratory tube. Generally, the gas analyzer comprises an infrared light source, entrance optics, a sample chamber, exit optics, and a detector assembly. The detector assembly may include one or more filters, one or more detectors, and a processor. During use of the apparatus, a gaseous stream is passed through the sample gas chamber to identify the presence and concentration one or more gases in the stream. For example, the gas stream may be a respiratory gas stream obtained from a patient, including carbon dioxide ($CO_2$) and one or more anesthetic or therapeutic agents in the patient's respiratory gases. These agents may include nitrous oxide, halothane, enflurane, desflurane, sevoflurane, and isoflurane, and other gases that absorb light at wavelengths having high rates of detection by the detector assembly.

In the case of a spectral gas analyzer, to determine accurately the light absorption characteristics and, hence, the composition, of a gas sample, it is useful to obtain a reference measurement under circumstances similar to the sample measurement. Such a reference measurement is useful for calibration purposes, to compensate for any system variances, and to facilitate digital processing. The reference measurement is obtained by illuminating a reference gas chamber that is evacuated, open to the ambient environment of the gas analyzer unit, or includes a known gaseous composition so as to yield information for determining the concentration of components of the sample gas. However, various aspects of the invention can be implemented without this preferred configuration.

Figure 1:
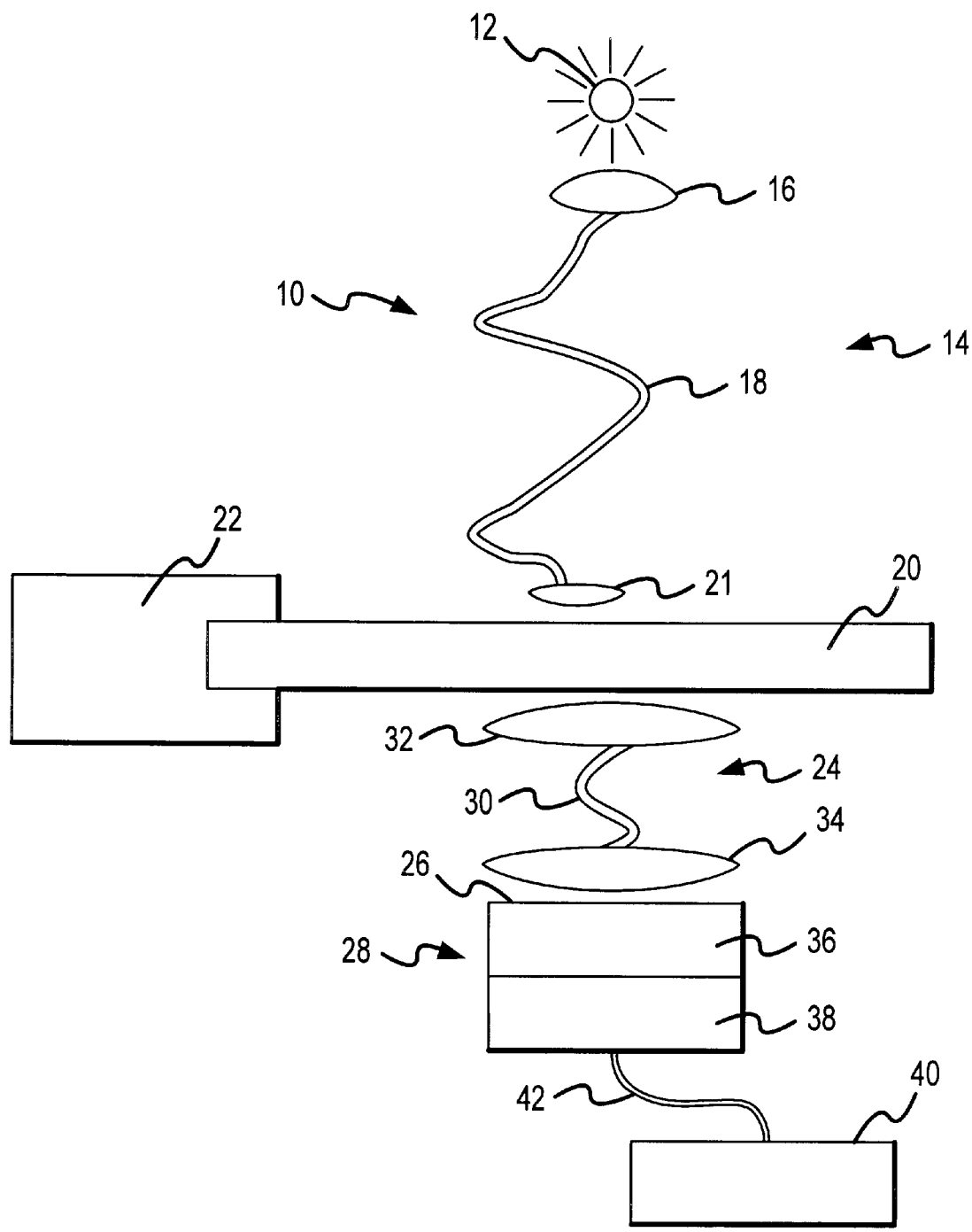
FIG. 1 is a schematic drawing of one embodiment of a gas analyzer of the present invention having a single optical path.

More specifically, one embodiment of a gas analyzer 10 in accordance with the present invention having a single optical path is illustrated in FIG. 1. Infrared light is produced by suitable source 12, which may be any source known in the art. Preferably, it is a polychromatic (black body) light source transmitting light dispersed across a predetermined wavelength range which includes absorption bands of one or more gaseous components of interest. Although various infrared wavelengths or spectra can be employed, source 12 preferably transmits light encompassing, for example, a wavelength range of about 2–12 microns. This wavelength range includes strong absorption bands of several respiratory/anesthetic components, such as nitrous oxide, halothane, enflurane, isoflurane, desflurane, and sevoflurane.

Examples of an appropriate source and other analyzer components are described in detail in U.S. patent application Ser. No. 08/605,973, entitled "OPTICAL SYSTEM WITH AN EXTENDED, IMAGED SOURCE" filed Feb. 23, 1996, which is incorporated by reference herein in its entirety. Thus, the source 12 may be an elongated strip and may include a heater element sandwiched between two emitter plates, with leads connected to a power source. To provide the desired illumination, the source 12 is preferably operated at a temperature greater than 900° C. to provide an improved signal to noise ratio and improved overall performance in the context of the illustrated high frequency chopped optical path gas analyzer. The elongate source, in combination with imaging optics, allows complete, substantially even, and intense illumination of the detector array for enhanced polychromatic analysis, as described below.

Entrance optics 14 is capable of transmitting light between source 12 and sample chamber 20, and may comprise conventional optics (e.g., lens 21), fiber optics, or a combination thereof. The use of fiber optics between the light source and the sample allows the source to be located some distance away from the gas chamber 20 and from the detector assembly 28. Further, the source 12 need not be in physical alignment with the chambers or the detector assembly. In some situations, it may be advantageous to place the source at a distance from the chamber and/or detector assembly, for example, to provide a more convenient work area around a patient or to avoid temperature fluctuations in the gases and the detector assembly during gas analysis.

As illustrated in FIG. 1, first lens 16 collects light output by source 12 and focuses the light onto fiber optics 18. First lens 16 may be any lens capable transmitting infrared light and of being connected optically to a fiber optics path. It is also possible to include one or more other optical elements, such as mirrors, prisms, diffraction devices, or filters to control or direct the infrared light.

Fiber optics 18 may comprise a single optical fiber or a bundle of optical fibers. Fiber optics 18 should be sufficiently flexible to allow for compact instrument design, and also suitable for use in proximity to the source, which may produce significant heat. Also, fiber optics 18 should be capable of transmitting light over the range of wavelengths of interest for analyzing the particular components which are present in the respiratory sample. Suitable chalcogenide glass fiber optics are manufactured by Amorphous Materials, Inc., 3130 Benton Street, Garland, Tex. 75047. Although not shown, additional optical elements may be inserted between fiber optics 18 and sample gas chamber 20.

The sample gas chamber 20 is incorporated into a conduit for a respiratory gas stream of a patient 22 such that the stream flows through chamber 20. Also, at least a part of the walls of chamber 20 is substantially transparent to infrared light over a substantial portion of the broad wavelength band transmitted through fiber optics 18, allowing light transmission through the chamber.

Gas analysis in accordance with the present invention may be enhanced by ensuring that the transmitted light reaches a much larger area of the filter surface 26 than would be illuminated simply by transmitting the beam, as it leaves the fiber optics 18, through the sample gas chamber 20. Thus, appropriate optical elements may be employed to spread and/or focus the light beam, either as it leaves the fiber optics 18, after it passes through sample chamber 20, or both. Also, the sample chamber 20 and the detector assembly 28 may be located remotely from one another, requiring additional optical elements, shown in FIG. 1 as exit optics 24, to collect, transmit, and spread light between sample chamber 20 and detector assembly 28. The exit optics may comprise conventional optics, fiber optics, or a combination thereof, as illustrated.

Light beams transmitted through fiber optics generally have small cross sections in a direction perpendicular to the propagation direction. However, a light beam will tend to spread after it leaves the end of a fiber optics light conductor, such as fiber optics 18. Thus, lens 32 functions to collect the beam after it has spread during transmission from the end of fiber optics 18 through sample chamber 20 and direct the beam into fiber optics 30. Lens 34 then spreads the light beam to provide even illumination of filter surface 26. There may also be one or more additional optical elements to redirect the light beam between sample gas chamber 20 and surface 26.

In accordance with the present invention, at least one of entrance optics 14 and exit optics 24 includes fiber optics. Entrance optics 14, sample chamber 20, and exit optics 24 are all capable of transmitting infrared light over at least a portion of the range of wavelengths produced by source 12. Preferably, they transmit light having wavelengths between about 2 and about 12 microns, and more preferably, between about 4 and about 10 microns.

The detector assembly 28 may include a polychromatic filter 36, a detector array 38, and a processor 40. Polychromatic filter 36 is utilized in conjunction with detector array 38 to allow for analysis of the incident light at multiple wavelengths or wavelength bands. Filter 36 is located downstream in the light path from sample chamber 20, preferably proximate to the detector array 38, as shown. The detector assembly 28 is capable of detecting infrared light over at least a portion of the range of wavelengths produced by source 12 and transmitted to the detector assembly 28.

Upon contacting the detector assembly, the light beam passes through a filter, such as 36. The filter may include one or more of several types of filters and light blocking devices, such as optical bandpass filters, which selectively pass light in a predetermined wavelength range while blocking wavelengths outside of the range, and optical masks, which block all light in selected wavelength bands.

Preferably, the filter includes a polychromatic filter which substantially simultaneously filters light passed by the optical mask and separates the incoming beam from the sample chamber into a plurality of spatially distributed beams, each including a narrow wavelength band. For example, a plurality of bandpass filters may be configured into a linear array to form a polychromatic filter, passing light in predetermined wavelength bands, with the range of wavelengths in each band being a function of position along the length of the polychromatic filter.

Preferred polychromatic filters include variable filters, having filtering characteristics that vary from one side of the filter to the other such that different wavelengths or wavelength ranges of the illumination are passed at different portions of the filter. More preferably, the filter has linearly varying filtering characteristics. The variable wavelength dependent transmission characteristics of the filter can be selected to allow for analysis at wavelengths where the gaseous components of interest have pronounced absorption bands or other identifying characteristics.

The instrument may also include a separate carbon dioxide filter which passes spectral wavelengths centered at about 4.26 micrometers, corresponding to an absorption band of $CO_2$. An optical grade sapphire filter is a preferred type of $CO_2$ filter. The $CO_2$ filter may abut the higher wavelength passing end of the polychromatic filter, is positioned in front of the $CO_2$ detector.

The detector array 38 is mounted downstream of the $CO_2$ filter, if present, and the polychromatic filter 36 in the light path. The detectors are located in the array so as to receive the narrow wavelength band light beams from the filter 36, and each detector functions to produce a signal having a magnitude that is proportional to the intensity of the light incident on each detector in the array; the light incident on each detector in the array is a function of the position of the detector below the linear variable filter and the $CO_2$ filter, if present. The detector array 38 is employed in conjunction with the polychromatic filter 36 so that the array elements provide intensity detection for multiple wavelengths or wavelength bands across a desired spectral range, for example 2–12 micrometers. The detector array 38 may include a single column of pyroelectric or heat sensitive elements for providing an electrical representation of the received light signal, and the array may be supported by a detector board carrying the circuitry for reading out the detector array, for example, serial clocking circuits. The detector array may be, for example, a 1 by N pyroelectric detector array.

By placing the detectors of array 38 at various sites along the length of the polychromatic filter 36, narrow passbands of light centered around selected wavelengths corresponding to absorption bands in one or more components of interest in the gas sample can be detected. The location of each detector defines the narrow wavelength band of light that is received from the gas sample chamber 20. Thus, specific individual detectors of the array 38 may be associated with specific wavelength bands of filter 36. The output from a particular individual detector of the detector array 38 which is associated with a particular filter portion or portions at a given time can, therefore, yield information concerning one or more specific gaseous components of interest. A polychromatic analysis of an incident beam can therefore be obtained by using processor 40 to correlate the output from a particular element, or group thereof, and the associated wavelength band.

The number of narrow wavelength light bands detected is simply a function of the number of light detectors placed along the length of polychromatic filter. To detect an additional band of light simply requires the addition of another detector at a site that corresponds to the desired wavelength of light. This configuration of elements minimizes the complexity of the apparatus and enables additions and changes to be made with relative simplicity.

The number of detectors in the array 38 is a function of the number of spectral measurements required to uniquely identify the set of components of interest and of the desired processing, e.g., any desired statistical analysis that can be accommodated by an overdetermined system. Acquiring additional spectral features of a gas sample provides increased analytical power. However, the entire absorption spectrum is concurrently gathered from a single respiratory gas sample, and, thus, the number of detectors is also a function of the desired spectral resolution for the individual detectors. Furthermore, the larger the number of spectral samples, the greater the span of the linear variable filter and, therefore, the greater the size of the gas sampling chamber and the slower the response time due to latency in gas transfer through the gas sample cell. The detector array may include, for example, about 73 detectors.

With regard to spectral resolution, the detector bandwidth is defined by the design of the polychromatic filter, the detector width, the proximity of the detector to the filter, and the angle of incidence of the light on the detector. The detector bandwidth selected for this application is preferably about 0.69% of the centered wavelength. Optionally, the detector array 38 may include preamplifier circuits which function to condition the signals generated by the detectors in the array 38 for transmission via electrical circuitry to processor 40.

The spectral information from the detector array 38 can be used by the processor 40 to determine gaseous composition information pertaining to multiple gaseous components. Thus, the illustrated system provides polychromatic analysis without the need to employ multiple detectors sequentially or to position multiple filters in the light path sequentially.

The processor may be integral with the detector array, or it may be a separate unit in electronic communication with detector array, such as via a cable or any other data transfer method known in the art. As shown in FIG. 1, the output information from detector array 38 is utilized by processor 40 to determine sample gas composition information by employing processing techniques such as digital absorption/transmissivity algorithms. Processor 40 can then output information regarding the presence and concentration of one or more gaseous components, as desired, on a substantially real time basis, such as in a visual display or data file, thereby allowing an anesthesiologist or technician to carefully monitor a patient's condition.

In operation, sample gas chamber 20, which is shown as a conduit, is connected to a respiratory gas stream, such as an exhaled stream from patient 22. The gas flows though sample gas chamber 20. At the same time, light from source 12 is collected by first lens 16 and transmitted via fiber optics 18. The beam passes through sample gas chamber 20 and exit optical unit 24 before impinging upon surface 26 of detector assembly 28. Within detector assembly 28, the light is filtered by polychromatic filter 36 before being received by detector array 38. Intensities of light incident on detector array 38 are converted by the individual detectors in array 38 into output signals, which are transferred to processor 40 via cable 42.

Figure 2:
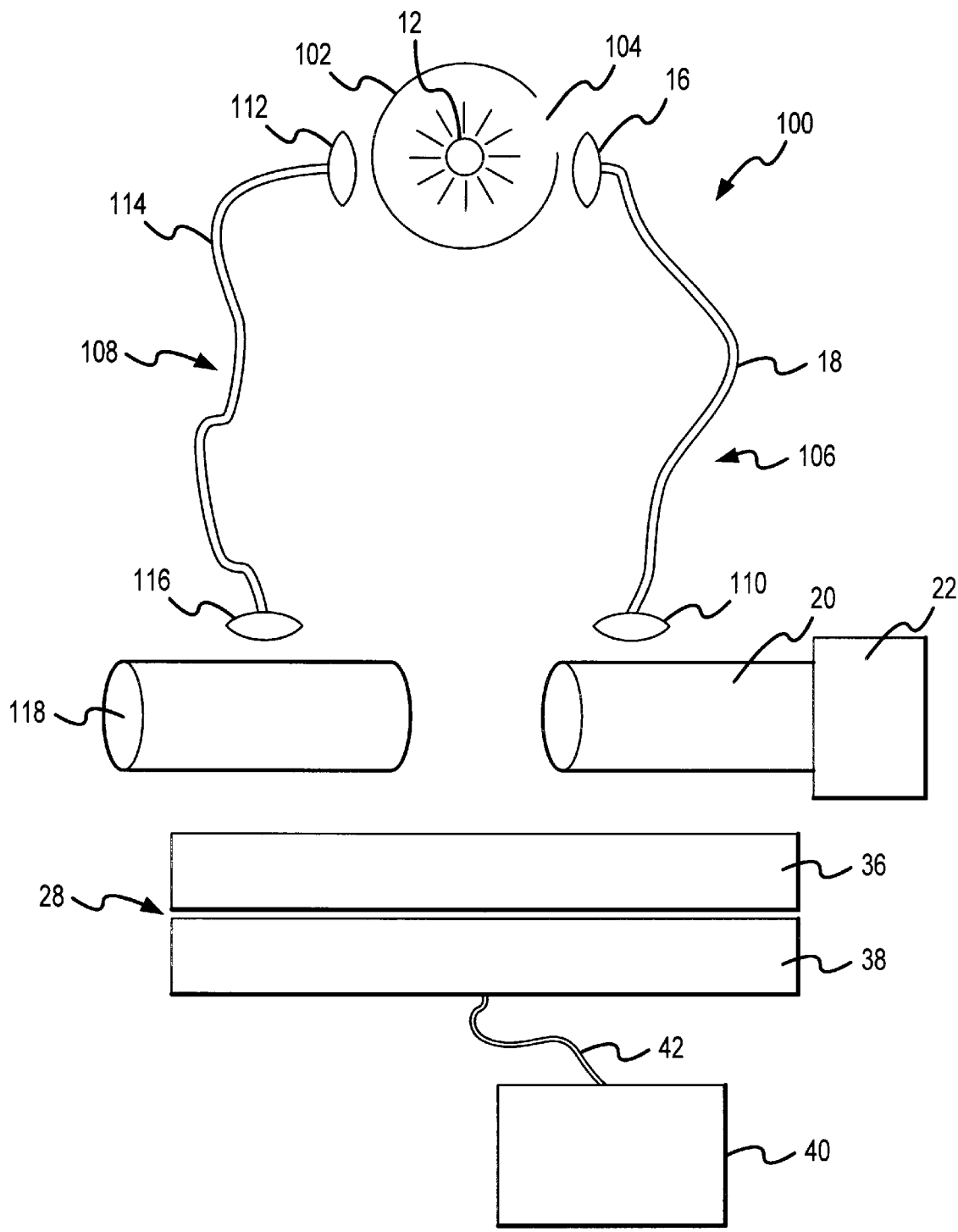
FIG. 2 is a schematic drawing of another embodiment of a gas analyzer of the present invention having dual optical paths.

A dual optical path embodiment 100 of the present invention is illustrated in FIG. 2. Elements that are the same as those in FIG. 1 have been assigned the same numbers. Also, in this embodiment, the source 12, the filter 36, and the detector array 38 are as described above with reference to FIG. 1.

The illustrated analyzer 100 includes a single broad band infrared source 12, a lens 16, a fiber optics 18, a sample gas chamber 20, and a detector assembly 28 as described above for the embodiment shown in FIG. 1. Incident light received from dual optical paths 106 and 108 is processed by a single detector assembly 26, comprising filter 34 and detector array 36. By using a single filter and a single detector array, undesired signal variances and instrument size requirements are reduced.

Source 12 is positioned within a concentric, rotatable, cylindrical beam chopper 102 having at least one pass-through window or slit 104 in a portion of the side wall thereof. As beam chopper 102 rotates, the window 104 allows light to reach sample optical path 106 and reference optical path 108 in an alternating manner. Alternatively, another mechanism, such as a prism could be used to split light output from source 12 into two beams. Preferably, for reasons which will become apparent below, the beam is split such that light reaches only one of the optical paths 106 and 108 at a time. The illustrated chopper 102 may include a single slit in its cylindrical sidewall.

In sample optical path 106, lens 16 gathers and focusses light from source 12 into sample fiber optics 18, which can transmit infrared light between source 12 and lens 110. Lens 110 disperses the light transmitted by sample fiber optics 18 so as direct the light through sample gas chamber 20 and focus an image of source 12 onto a polychromatic filter 36. Sample gas chamber 20 is positioned in a stream respiratory gas conduit, as described for the embodiment 10 illustrated in FIG. 1.

Reference optical path 108 includes a lens 112 which can gather and focus light from source 12 into reference fiber optics 114. Fiber optics 114 can transmit light between lens 112 and lens 116, which operates to disperse light transmitted through the fiber optics 114 and direct the light through reference chamber 118 and focus an image of source 12 onto filter 36. Reference chamber 118 may be evacuated, or it may contain a gas of known composition. Chamber 118 may be sealed, or the gas may flow through it.

Processor 40 is capable of receiving the electronic output from the detector array 38, such as via cable 42, and creating a display in substantially real time to allow qualitative and/or quantitative determination of the sample gas composition. Processor 40 also can compare the signals received via sample optical path 106 and reference optical path 108.

Further, processor 40 can be synchronized with the rotation of chopper 102. A read out clocking of the detector array 38 can be readily coordinated with the rotation rate of chopper 102 to provide alternate sample and reference values. Such coordination may be accomplished, for example, by indexing the read out clocking to pulses from an encoder or motor associated with the chopper 102. Interval clocking may be more convenient if source 12 and lenses 16 and 112 are geometrically arranged in a substantially linear relationship, with lenses 34 and 112 located about 180° apart relative to source 12. This arrangement allows for convenient variable duty cycle usage by appropriate chopper operation and detector cycling.

To further facilitate comparison of the signals received via the two optical paths, optical elements 16, 18, 110, 112, 114, and 116 are preferably such that the signals produced by detector array 38 for light intensities received via the two light paths are readily comparable. Preferably, the equivalent optical elements in the two paths are identical or similar. It will be appreciated that the chambers 118 and 20 may be spatially separated by use of fiber optics between the source 12 and chambers 118 and 20, and/or between the chambers 118 and 20 and detector assembly 28.

During use of apparatus 100, a gaseous stream is passed through the sample gas chamber 20 to identify the presence and concentration of one or more gases in the stream. In operation, infrared source 12 emits light which, by virtue of the rotation of chopper 102 allows infrared light beams to alternately pass through the window or slit 104 and impinge on lenses 16 and 112, respectively. The light beams are transmitted via sample and reference fiber optics 18 and 114, respectively, and then illuminate sample gas chamber 20 and reference gas chamber 118, respectively, before impinging on filter 36 and detector array 38. To detect the intensities of a broad range of selected wavelengths, the optical paths 106 and 108 are designed to focus the light from source 12 onto the detector array 38. The detector array 38 is thereby substantially completely illuminated, and source energy losses are minimized. In this regard, in the illustrated embodiment 100, filter 36 and detector array 38 are arranged in an aligned upstanding orientation. As will be appreciated, the gas analyzer configuration, selected wavelengths, and various other factors can be varied depending upon parameters such as space requirements and the transmissivity/ absorption characteristics of the gaseous component or components of interest. The apparatuses shown in FIGS. 1–2 can be enclosed in appropriate enclosures, cases, or housings, either with all components in a single enclosure or with components divided among a plurality of enclosures. Preferably, the enclosure or enclosures about the chamber or cells, the filter, and the detector array comprise a light absorptive material having a low coefficient of thermal conductivity. Most preferably, the material is selected from ceramics, such as black alumina and composites thereof.

Referring to FIG. 3, the entrance and exit fiber optics 210 and 212, respectively, may be combined to form a probe 200 which can be removably secured to a breathing conduit or tube 214. A portion of the wall of tube 214 is substantially transparent to infrared light. For example, the tube may be formed from a material which is transparent to infrared light, or there may be a pair of windows 216 and 218 on opposite sides of the tube wall, as illustrated. The windows 216 and 218 may comprise an infrared-transparent material, or they may be holes in the tube wall. Preferably, windows 216 and 218 are spaced apart a predetermined distance suitable for analysis of the gas in tube 214. Probe 200 is adapted to clamp onto or seal against tube 214 so that the tube wall and the ends of fiber optics elements 210 and 212 are in a predetermined and reproducible spatial relationship with each other. Fiber optics 210 and 212 may also include lenses or other conventional optical elements. Entrance and exit fiber optics 210 and 212 are shown in FIG. 3 as two separate, side-by-side light guides. Alternatively, one light guide may surround the other in a concentric arrangement. For example, the exit fiber optics light guide may surround the entrance fiber optics light guide because the light beam transmitted by the entrance optics 210 will tend to spread as it passes through the interior of tube 214, resulting in a larger cross sectional area for the light beam received by exit optics 212.

Figure 3A:
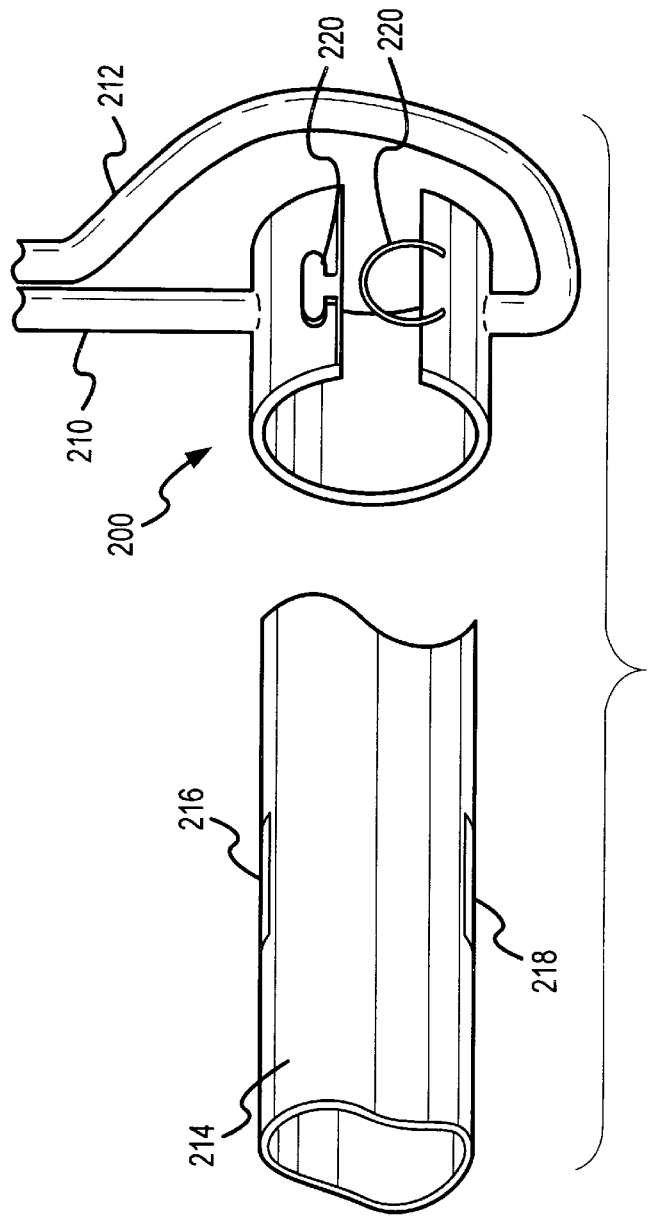
FIG. 3 is a perspective view of a fiber optics probe in accordance with the present invention, shown alongside a respiratory gas tube in FIG. 3(a) and assembled with the tube in FIG. 3(b)
Figure 3B:
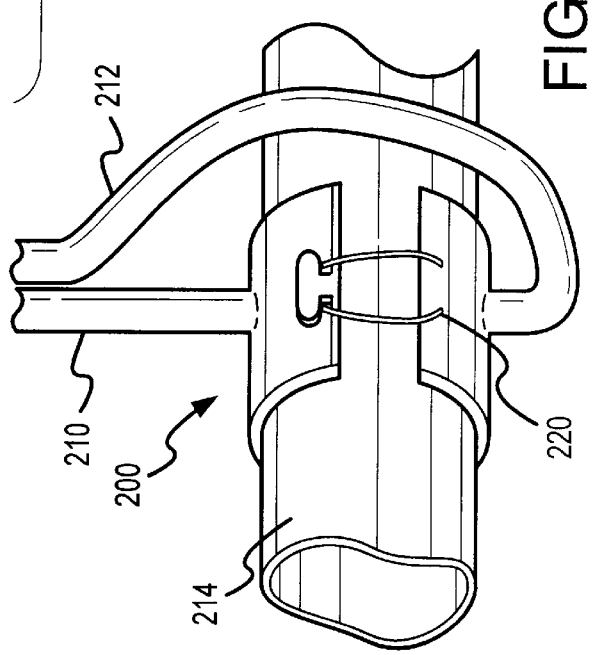

In use, probe 200 is secured to tube 214, as shown in FIG. 3(b). As shown, a clamping mechanism 220 secures the probe 200 around tube 214. However, the probe 200 may be secured to the tube by any suitable manner known in the art which allows the fiber optical elements 210 and 214 to be aligned with the windows in a desired and reproducible spatial arrangement. For example, the entrance and exit fiber optics 210 and 212 may be mounted on separate mounting elements that are interconnected for substantially linear movement of the mounting elements towards or away from one another, e.g., by sliding motion on parallel rods. In this manner, such elements may accommodate different sized breathing circuit conduits while maintaining the desired optical alignment of elements 210 and 212. Light is transmitted by entrance fiber optics element 210 from a source (not shown) to window 216, which is covered by part of probe 200 in FIG. 3(b). The light which passes through window 214, the interior of tube 214, and window 218, and is then received by exit fiber optics element 212 for transmission to a detector (not shown). A portion of the light from entrance fiber optics 210 is absorbed by gaseous components within tube 214. After use, probe 200 is detached from tube 214, as shown in FIG. 3(a). Tube 214 may be discarded or cleaned for re-use.

Figure 4:
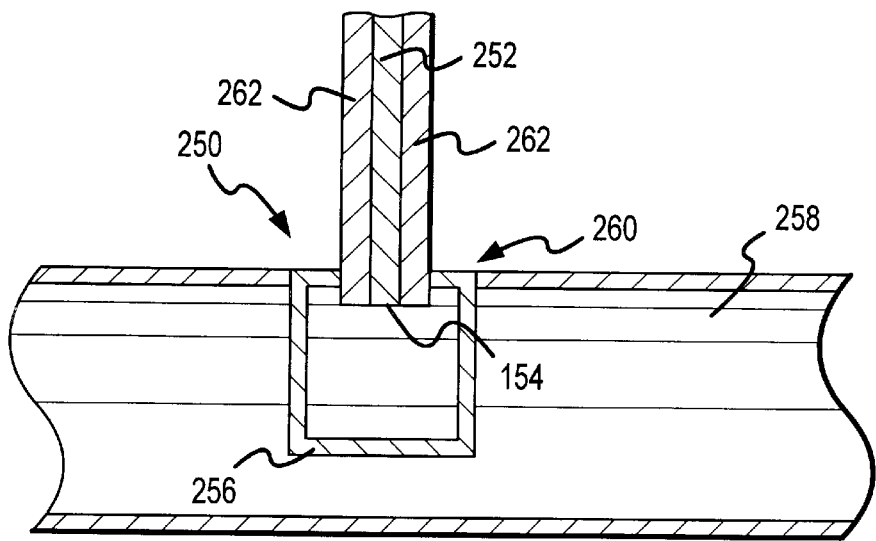
FIG. 4 is a cross sectional view of another fiber optics probe in accordance with the present invention.

In another embodiment of the present invention, shown in FIG. 4, probe 250 includes entrance fiber optics 252, terminating in end 254, and a mirror 256 secured at a known distance from the end 254. The distance is selected to provide an appropriate path length for detecting the gaseous components of interest in tube 258. Probe 250 is detachably secured to tube 258, with mirror 256 extending into a hole 260 in the wall of tube 258. Exit fiber optics 262 is disposed about entrance fiber optics 252 in a concentric arrangement.

It should be appreciated that mirror 256 is a device which is highly reflective for infrared light over the wavelength range of interest, but is not necessarily a conventional mirror capable of reflecting visible wavelength light. Also, mirror 256 may be disposable, with a mounting mechanism which provides reproducible positioning of the mirror relative to the entrance and exit optics. The use of a mirror which can be thus positioned reproducibly reduces or eliminates the need to recalibrate the optical system prior to each use.

Probe 250 may be secured to tube 258 in any manner which prevents excessive leakage of respiratory gases from tube 258 and which maintains the desired spacing between end 254 and mirror 256. For example, probe 250 and tube 258 may be joined by one or more friction fittings, or they may be molded so they snap together, or probe 250 may be clamped around tube 258. Such an arrangement, which allows the tube and the probe to be easily detached from one another after use, facilitates cleaning of the tube without subjecting the optics to wear and tear and contact with cleaning chemicals. Alternatively, the tube may be disposable.

In use, probe 250 is secured to tube 258. Light from a source is transmitted via entrance fiber optics 252 to tube 258 and reflected by mirror 256 back through tube 258 for transmission via exit fiber optics 262 to a detector (not shown).

Figure 5:
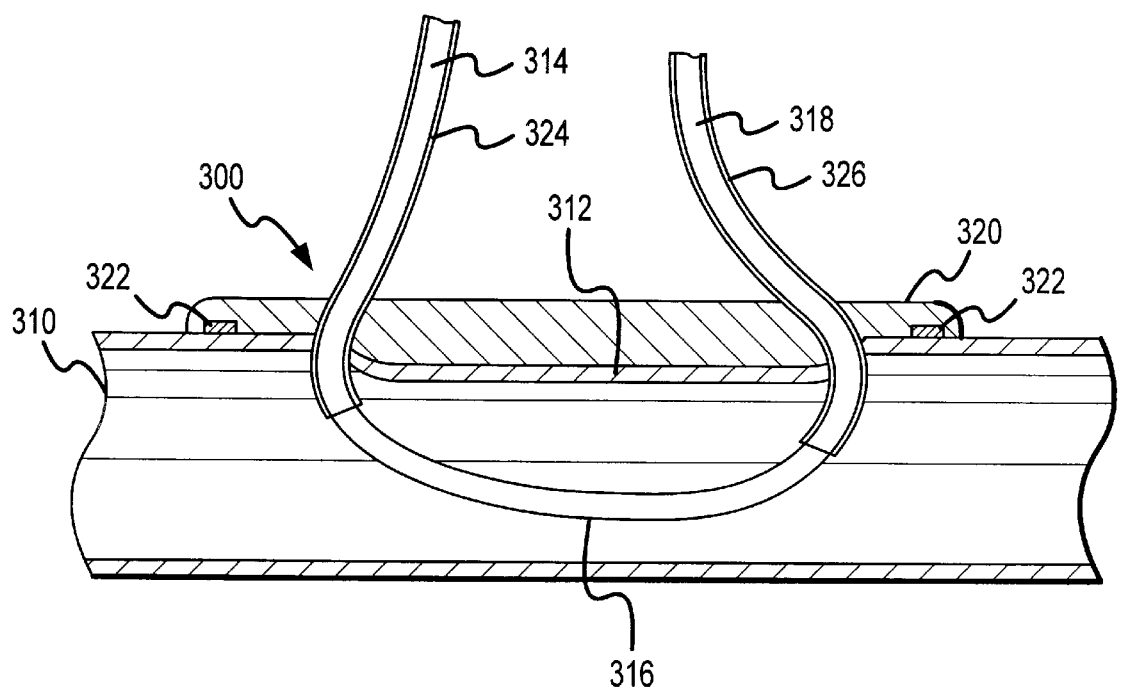
FIG. 5 is a cross sectional view of yet another fiber optics probe in accordance with the present invention.

Another type of probe according to the present invention is shown generally as 300 in FIG. 5. Tube 310 has a longitudinal slot 312 in its wall. Probe 300 includes entrance optics 314, an unshielded fiber optics light guide 316 which extends through slot 312 and longitudinally through part of tube 310, and exit optics 318. Probe 300 can be sealed to the wall of tube 310 to prevent gas loss through slot 312. As shown, probe 300 includes a cover portion 320 which is sealed against the exterior surface of tube 310, such as with elastomeric seal 322. Any suitable means of sealing the probe against the tube can be used, provided that the probe cannot move significantly relative to the tube during gas analysis and significant leakage of gas through slot 312 is prevented. As alternatives to the longitudinal slot 312, the guide 316 may be threaded through a length of the tube 310 from one opening to another, or may extend through the tube (directly or in wound/serpentine fashion) from one side to another. In any case, the section of tube with the guide may be provided as a probe unit for interposition within a respiratory conduit.

Entrance optics 314 and exit optics 318 are both illustrated as shielded fiber optics light conductors, although they could also be conventional optical assemblies. Cladding 324 and 326 shield entrance optics 314 and exit optics 318, respectively, outside of the tube 310 to prevent light from exiting the light guides through the sides of the light guides. In contrast to entrance optics 314 and exit optics 318, unshielded fiber optics 316 is exposed to the sample gas along its length, such that light transmitted from entrance optics 314 to exit optics 318 is alternated due to optics/gas interface phenomena in a manner that can be correlated to gas composition.

Figure 6:
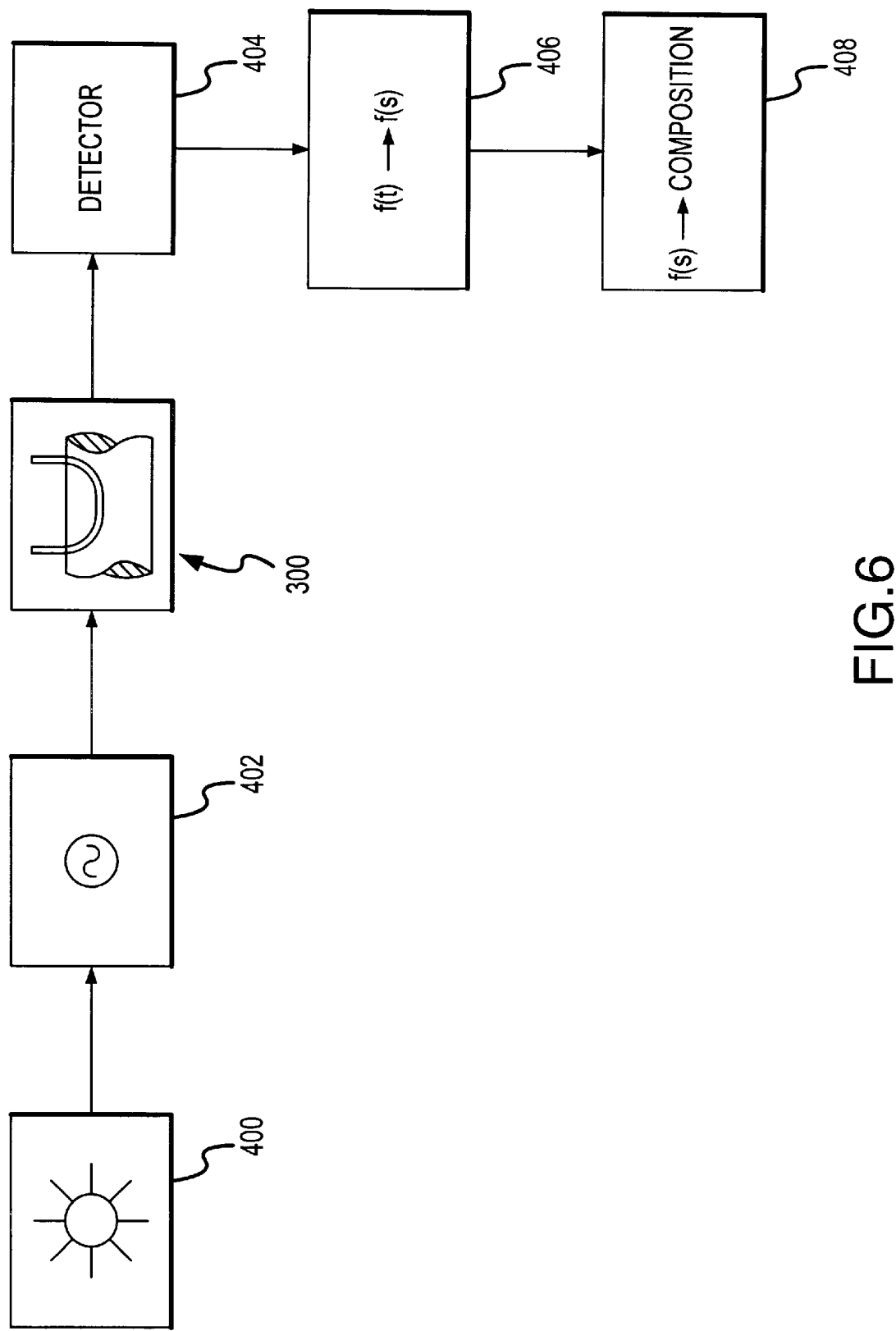
FIG. 6 is a schematic diagram of an analyzer in accordance with the present invention.

Referring to FIGS. 5 and 6, in use, probe 300 is secured to tube 316. Infrared light is transmitted by source 400 and modulated by modulator 402 to provide a modulated optical signal. The modulator 402 may include fixed mirrors, moving mirrors filters or the like, for modulating the transmitted optical signal such that the signal has an intensity that varies over time in a controlled manner, e.g., a square wave or other sinusoidal pattern. As light is transmitted between the source 400 and a detector 404 via entrance optics 314, unshielded fiber optics 316, and exit optics 318, the light is attenuated in the unshielded fiber optics 316 due to interaction at the interface between the fiber optics and the gas. At the interface between the gas and the unshielded fiber optics 316, interaction of the guide/light with the gas results in detectable variations in the attenuation of the light which is transmitted through the fiber optics. These attenuation variations are dependent upon the composition of the gas sample, and can be empirically and/or theoretically correlated to particular composition values, e.g., concentrations of particular components of interest.

In this regard, the light source is transmits illumination in the near or mid-infrared wavelength range. For example, the source may transmit light having a wavelength of 720 and/or 1020 nanometers. Also preferably, the light intensity is modulated, with a repeat interval or period which is preferably in the millisecond range. The signal can be monitored for a time sufficiently long to detect changes in attenuation of associated signal changes due to the interactions occurring at the interface.

A preferred way to monitor the attenuation variations is with Fourier transform analysis, wherein the received optical signals are transformed (406) from the time domain to the frequency domain. In this regard, only one detector is needed. A suitable detector is a PbSe detector. The Fourier transform analysis can be performed substantially in real time and yields a series of values at given frequencies or wavelengths. This set of values can be correlated particular compositions based on a calibration procedure involving analysis of gases of known compositions.

The use of fiber optics allows the source to be in a separate enclosure from the sample chamber and, if present, the reference chamber. Also, the detector may be separated from the gas chamber or chambers and the processor. Separating the source from the chambers and the detector may be advantageous because it may improve the temperature stability of the cells and the detector. Also, separation of the components may decrease clutter and crowding in the work area adjacent a patient, such as during a medical procedure.

While specific embodiments of this invention has been disclosed, it is expected that those skilled in the art can and will design alternate embodiments of this invention that fall within the scope of the appended claims.

What is claimed is:

1. An apparatus for monitoring the composition of a main respiratory gas stream of a patient, said apparatus comprising:
   a broad band infrared source capable of producing infrared light having a spectral content distributed at least across a wavelength range from about 4 microns to about 8 microns;
   means for detecting infrared signals at a plurality of wavelengths within said wavelength range; and
   means for transmitting light between said broad band infrared source and said means for detecting, said light being transmitted at least partially through a respiratory gas conduit outside the patient such that said main respiratory gas stream at said patient can be analyzed free from the need to divert a side stream therefrom for purposes of composition analysis, the main respiratory gas the conduit being adapted for flow of the main respiratory gas stream therethrough, said means for transmitting including fiber optics for transmitting infrared light within said wavelength range.

2. An apparatus according to claim 1, wherein said means for transmitting includes a fiber optics light guide capable of transmitting infrared light between said source and said conduit.

3. An apparatus according to claim 1, wherein said means for transmitting includes a fiber optics light guide capable of transmitting infrared light between said conduit and said means for detecting.

4. An apparatus according to claim 3, wherein:
   said conduit includes a wall portion outside said patient;
   said wall portion includes first and second opposed windows which allow infrared light transmission across said conduit; and
   said means for transmitting light transmits light across said conduit through said windows.

5. An apparatus according to claim 1, wherein:
   said conduit includes a wall portion outside said patient, said wall portion including a window;
   said means for transmitting includes an end portion and means for reflecting infrared light, said means for reflecting spaced apart from said end portion so as to provide a two-directional pathway for light transmission between said end portion and said means for reflecting, said end portion adapted for releasable engagement with said wall portion at said window such that said means for reflecting is positioned inside said conduit; and
   said means for transmitting transmits light between said broad band infrared source and said means for reflecting and between said means for reflecting and said means for detecting.

6. An apparatus according to claim 1, wherein:
   said conduit includes a wall portion outside said patient, said wall portion including first and second opposed windows which allow infrared light transmission across said conduit;
   said means for transmitting including support means for supporting, in predetermined spatial relationship, an end portion and means for reflecting infrared light, said means for reflecting spaced apart from said end portion so as to provide a two-directional pathway for light transmission through said conduit via said windows, said support means adapted for engaging with said conduit adjacent said wall portion such that said end means is positioned adjacent said first window and said means for reflecting is positioned adjacent said second window; and
   said means for transmitting transmits light from said broad band infrared source through said first window to said means for reflecting and from said means for reflecting to said means for detecting.

7. An apparatus according to claim 1, wherein:
   said conduit includes a wall portion outside said patient, said wall portion including at least one window; and
   said means for transmitting includes an unshielded fiber optics portion which is insertable into said conduit through the at least one window, said unshielded portion capable of allowing interaction of infrared light with said gas in said conduit.

8. An apparatus according to claim 1, wherein said infrared source produces light having a continuum of infrared wavelengths.

9. An apparatus according to claim 8, wherein said continuum extends between about 4 microns and about 10 microns.

10. An apparatus according to claim 8, wherein said continuum extends between about 2 microns and about 12 microns.

11. An apparatus according to claim 1, wherein said means for detecting comprises:
    at least one filter capable of filtering incident light on a wavelength dependent basis; and
    at least one detector element capable of receiving filtered light from said filter.

12. An apparatus according to claim 1, further comprising an analyzer for providing information regarding the concentration of carbon dioxide and at least one of nitrous oxide, halothane, enflurane, sevoflurane, desflurane, and isoflurane.

13. An apparatus for monitoring the composition of a respiratory gas stream of a patient, said apparatus comprising:
    a broad band infrared source capable of producing infrared light having a spectral content distributed at least across a wavelength range from about 4 microns to about 8 microns;
    means for detecting infrared signals at a plurality of wavelengths within said wavelength range;
    means for transmitting light between said broad band infrared source and said means for detecting, said light being transmitted at least partially through a respiratory gas conduit outside the conduit being adapted for flow of the respiratory gas stream therethrough, said means for transmitting including fiber optics for transmitting infrared light within said wavelength range; and
    a reference light path including fiber optics, and wherein said means for detecting infrared signals includes means for comparing infrared signals received via said means for transmitting to signals received via said reference light path.

14. An apparatus for monitoring the composition of a main respiratory gas stream of a patient, said apparatus comprising:
    an infrared light source;

a detector assembly capable of detecting infrared light having wavelengths produced by said source, said detector assembly including means for separately detecting infrared light within a plurality of infrared wavelength bands, each said band having a unique spectral content; and transmission means for transmitting infrared light from said infrared source between said infrared source and said means for detecting, said transmission means including fiber optics for transmitting said infrared light wherein said infrared light is transmitted at least partly through a main respiratory gas conduit outside said patient such that said main respiratory gas stream at said patient can be analyzed free from the need to divert a side stream therefrom for purposes of composition analysis, said main respiratory gas conduit having a wall portion for transmitting infrared light produced by said infrared source.

15. An apparatus according to claim 14, wherein said infrared light source is a broad band infrared source having a spectral content distributed at least across a wavelength range from about 4 microns to about 8 microns.

16. An apparatus according to claim 14, further comprising means for reflecting infrared light, said means for reflecting being positionable within said conduit.

17. An apparatus according to claim 14, wherein:
said conduit includes two opposed windows for transmitting light; and
said apparatus further comprises means for reflecting infrared light, said means for reflecting being positionable outside said conduit adjacent one of said windows, wherein light is transmitted through said wall portion and said gas inside said conduit and reflected back through said wall portion and said gas.

18. An apparatus for monitoring multiple components in a main respiratory gas stream of a patient, said apparatus comprising:
means for receiving said main respiratory gas stream, said means adapted to allow said main respiratory gas stream to flow therethrough and also adapted for infrared spectroscopy of a gas located therein such that said main respiratory gas stream at said patient can be analyzed free from the need to divert a side stream therefrom for purposes of composition analysis;
an infrared source;
means for detecting infrared light transmitted through said means for receiving and said respiratory gas stream and for characterizing said respiratory gas stream relative to multiple gaseous components present in said respiratory gas stream;
means for transmitting light between said infrared source and said means for receiving and between said means for receiving and said means for detecting, said means for transmitting including fiber optics operative to transmit infrared light.

19. An apparatus according to claim 18, wherein said infrared source is a broad band source having a spectral content distributed at least across a wavelength range from about 4 microns to about 8 microns.

20. An apparatus according to claim 18, wherein said means for detecting is capable of detecting infrared signals at multiple wavelengths indicative of quantities of said multiple components present in said means for receiving.

21. An apparatus according to claim 18, wherein:
said means for transmitting includes an infrared fiber optics light guide having an unshielded portion inside a respiratory gas conduit;

said means for detecting includes means for detecting said infrared light after transmission through said fiber optics light guide and determining composition information based on interactions with said respiratory gas at an interface between said light guide and said gas.

22. An apparatus according to claim 21, wherein said means for detecting includes means for performing Fourier transform analysis on light transmitted through said fiber optics light guide.

23. An apparatus according to claim 21, further comprising means for modulating light from said infrared source to provide an infrared signal for transmission via said means for transmitting.

24. An apparatus for monitoring the composition of a main respiratory gas stream of a patient, said apparatus comprising:
probe means for transmitting infrared light to and from a main respiratory gas conduit for receiving said main respiratory gas stream such that said main respiratory gas stream at said patient can be analyzed free from the need to divert a side stream therefrom for purposes of composition analysis, said probe means supporting first means for transmitting said infrared light into said main respiratory gas conduit and second means for receiving the infrared light transmitted into said main respiratory gas conduit;
said probe means including infrared fiber optics for transmitting said infrared light and coupling means for coupling said probe means to said main respiratory gas conduit such that said infrared light is transmitted through said main respiratory gas stream and returned from said main respiratory gas conduit by said probe means for use in analysis.

25. An apparatus according to claim 24, wherein said probe means includes means for reflecting infrared light and having a two-directional light path between said fiber optics and said reflecting means.

26. An apparatus according to claim 24, wherein:
said probe means includes an unshielded fiber optics light guide, said unshielded light guide being positionable substantially inside said main respiratory gas conduit.

27. A method for monitoring multiple components in a main respiratory gas stream of a patient, said method comprising:
receiving said main respiratory gas stream in a conduit adapted to allow said main respiratory gas stream to flow therethrough such that said main respiratory gas stream at said patient can be analyzed free from the need to divert a side stream therefrom for purposes of composition analysis;
transmitting light between an infrared source and said conduit and between said conduit and a means for detecting, said transmission being via means for transmitting including fiber optics operative to transmit infrared light; and
detecting infrared light transmitted through said means for receiving and said respiratory gas stream and analyzing said detected infrared light relative to multiple gaseous components.

28. A method according to claim 27, wherein:
said transmitting step includes modulating said infrared light to provide a modulated optical signal and transmitting said modulated signal via an infrared fiber optics light guide having an unshielded portion inside said conduit.

29. A method according to claim 27, wherein said analyzing step includes performing Fourier transform analysis on light transmitted through said fiber optics light guide.

30. A method for monitoring multiple components in a respiratory gas stream of a patient, said comprising:

receiving said respiratory gas stream in a conduit adapted to allow said respiratory gas stream to flow therethrough;

transmitting light between an infrared source and between said conduit and a means for detecting, said transmission being via means for transmitting includes fiber optics operative to transmit infrared light;

detecting infrared light transmitted through said means for receiving and said respiratory gas stream and analyzing said detected infrared light relative to multiple gaseous components; and comparing light transmitted through said means for receiving with a reference light measurement.

31. A method according to claim 27, wherein said step of transmitting comprises:

providing infrared light having a spectral content distributed at least across a wavelength range from about 4 microns to about 8 microns.

32. A method according to claim 27, wherein said transmitting step comprises:

transmitting light through a wall portion of said conduit, said wall portion including first and second opposed windows which allow infrared light transmission across said conduit.

33. A method according to claim 27, wherein said transmitting step comprises:

transmitting light through a wall portion of said conduit;

reflecting said transmitted light with a reflecting means; and receiving said reflected light for transmission to said detecting means.

34. A method according to claim 27, wherein said detecting step comprises:

filtering light received by said means for detecting, said filtering being on a wavelength dependent basis; and detecting filtered light received through said filter.

35. A method according to claim 27, wherein:

said respiratory gas comprises carbon dioxide and at least one component selected from nitrous oxide, halothane, enflurane, sevoflurane, desflurane, and isoflurane; and said analyzing step comprises providing information regarding the concentration of said at least one component.

36. A method according to claim 30, wherein said step of comparing comprises:

providing a reference light path including fiber optics;

detecting reference infrared signals transmitted over said reference light path; and comparing infrared signals received via said means for transmitting to signals received via said reference light path.

* * * * *

UNITED STATES PATENT AND TRADEMARK OFFICE
CERTIFICATE OF CORRECTION

PATENT NO. : 6,039,697
DATED : March 21, 2000
INVENTOR(S) : WILKE, et al.

It is certified that error appears in the above-indentified patent and that said Letters Patent is hereby corrected as shown below:

At Column 15, Claim 1, line 20, before the word "respiratory", insert the word --main--;
At Column 15, Claim 1, line 25, after the word "gas", delete the word --the--;
At Column 19, Claim 30, line 6, after the word "and", delete the word --between--.

Signed and Sealed this

Twentieth Day of March, 2001

Attest:

NICHOLAS P. GODICI

*Attesting Officer*   *Acting Director of the United States Patent and Trademark Office*